United States Patent
Farzin-Nia et al.

[11] Patent Number: 6,042,374
[45] Date of Patent: Mar. 28, 2000

[54] SELF LIGATING ORTHODONTIC BRACKET

[75] Inventors: Farrokh Farzin-Nia, Inglewood, Calif.; Rohit C. L. Sachdeva, Plano, Tex.; Thomas V. Selkee, Claremont, Calif.

[73] Assignee: Ormco Corporation, Orange, Calif.

[21] Appl. No.: 09/007,120

[22] Filed: Jan. 14, 1998

[51] Int. Cl.[7] .................................................. A61C 3/00
[52] U.S. Cl. ............................................. 433/13; 433/15
[58] Field of Search ............................. 433/10, 13, 11, 433/14, 15, 21, 8

[56] References Cited

U.S. PATENT DOCUMENTS

| | | | |
|---|---|---|---|
| 2,548,864 | 4/1951 | Brusse | 433/11 |
| 3,772,787 | 11/1973 | Hanson | 32/14 |
| 3,878,609 | 4/1975 | Wallshein | 433/15 |
| 4,212,638 | 7/1980 | Korn | 433/8 |
| 4,248,588 | 2/1981 | Hanson | 433/11 |
| 4,492,573 | 1/1985 | Hanson | 433/11 |
| 4,522,590 | 6/1985 | Pletcher | 433/15 |
| 4,725,229 | 2/1988 | Miller | 433/11 |
| 5,356,288 | 10/1994 | Cohen | 433/8 |
| 5,399,088 | 3/1995 | Mechley | 433/20 |
| 5,429,501 | 7/1995 | Farzin-Nia | 433/21 |
| 5,540,586 | 7/1996 | Hanson | 433/22 |
| 5,630,716 | 5/1997 | Hanson | 433/14 |
| 5,685,711 | 11/1997 | Hanson | 433/11 |
| 5,885,074 | 3/1999 | Hanson | 433/13 |

*Primary Examiner*—Ralph A. Lewis
*Attorney, Agent, or Firm*—Wood, Herron & Evans, L.L.P.

[57] ABSTRACT

A self-ligating orthodontic bracket comprised of a ligating member containing a coil spring segment for extending the ligating member over an archwire or retainer wire and over one or more tie wings to secure the archwire or retainer wire in the bottom of a slot in the bracket. The ligating member containing the coil spring may have ends that are engaged in opposing mesially-distally extending bores in one side of the bracket body, with the ligating member being engaged with one or more tie wings on an opposite side of the bracket body. Alternatively, the ligating member may form a closed loop with the ligating member engaged under both occlusally-projecting and gingivally-projecting tie wings or engaged under one or more tie wings on one side of the bracket body and passing through a mesially-distally extending bore on the opposite side of the bracket body.

30 Claims, 3 Drawing Sheets

SELF LIGATING ORTHODONTIC BRACKET

FIELD OF THE INVENTION

The present invention relates to a combination orthodontic bracket and ligating member for retaining an archwire or retainer wire in an archwire slot of the bracket.

BACKGROUND OF THE INVENTION

Ligation of an archwire to an orthodontic bracket is one of the most time consuming and frequently repeated procedures that is practiced during orthodontic treatment. Ligation typically has been performed using elastic "O" rings or soft stainless steel ligature ties. The placing and removing of "O" rings and ligature ties are time-consuming and tedious tasks which increase patient chair side time and expense. In general in these procedures the archwire is first inserted into the archwire slots of the brackets, which are already fixed to the teeth. The archwire is then locked into the slots by placing the ligation member over the archwire and engaging one or more tie wings to thereby securely hold the archwire in place. The ligature is intended to continuously force the archwire to the bottom of the slot.

In various types of brackets it is the bottom of the slot which is configured to align the teeth in their correct position along the continuous length of the archwire. Hence, if the ligature does not continuously force the archwire to the bottom of the slot, the alignment of the teeth may be compromised. One drawback of elastic "O" rings is that they tend to lose their elasticity in a very short period of time, so that the force needed to secure the archwire in the bottom of the slot is no longer present. Thus, the archwire is able to rotate, resulting in an undesirable alignment. To avoid this result, elastic "O" ring ligatures must be replaced quite frequently. Similarly, soft stainless steel ligature ties tend to rapidly lose their retentive forces on the archwire and also must be replaced frequently.

Alternatively, there are various bracket designs that have attempted to eliminate the need for a ligature altogether. For example, "Activa" produced by A Company, "Speed" and "Edgelock" produced by Ormco Corporation, and others are typical examples of ligature-less brackets that are commercially available. All of the above examples, although facilitating orthodontic procedures, have compromised certain design features of the bracket. For example, slot cavities have been designed to have a certain fixed size that is necessarily greater than the largest possible orthodontic wire commercially available; self ligation features add to the overall height of the bracket, making it more uncomfortable for the patients; and the locking mechanisms in the self ligation systems significantly limit the possibility of providing other desirable features, such as hooks, on the bracket.

Therefore, what is needed is a self-ligating bracket which overcomes the various drawbacks mentioned above and provides sustained archwire-retaining forces during the course of orthodontic treatment.

SUMMARY OF THE INVENTION

In its broadest aspects, the present invention provides an orthodontic bracket having a ligating member containing at least one coil spring segment, in which the ligating member is configured to continuously force an archwire or retainer wire to the bottom of the slot. This results in a smaller, more comfortable bracket that may be quickly ligated and may include additional features, such as hooks, if desired. To this end, and in accordance with the principles of the present invention, the bracket body has a mesially-distally extending slot for receiving an archwire or retainer wire and includes a ligating member that forms a closed loop and contains a coil spring segment. The coil spring section of the ligating mechanism provides extension so that the ligating member may be stretched over the tie wings and the archwire or retainer wire. Subsequent to ligation, the coil spring segment will provide a continuous force that keeps the archwire or retainer wire in the bottom of the slot. Thus, the alignment of the teeth will not be compromised by rotation of the bracket due to a loosely retained archwire or retainer wire.

A further advantage of the invention is that the self ligating mechanism does not add considerably to the overall height of the bracket. Thus, patient comfort is maintained. Furthermore, the configuration of the ligating mechanism does not prevent the inclusion of other design features, such as hooks, on the bracket body. Yet another advantage is that the invention is suitable for both lingually- and labially-applied brackets.

By virtue of the foregoing, there is thus provided a smaller, more comfortable orthodontic bracket having one or more tie wings, additional features, such as hooks, if desired, and a self ligating member containing at least one coil spring segment that may be quickly stretched over the archwire or retainer wire and tie wings, and which continuously forces the archwire or retainer wire to the bottom of the slot.

These and other objects and advantages of the present invention shall become more apparent from the accompanying drawings and description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the principles of the invention.

DETAILED DESCRIPTION OF THE INVENTION

Figure 1:
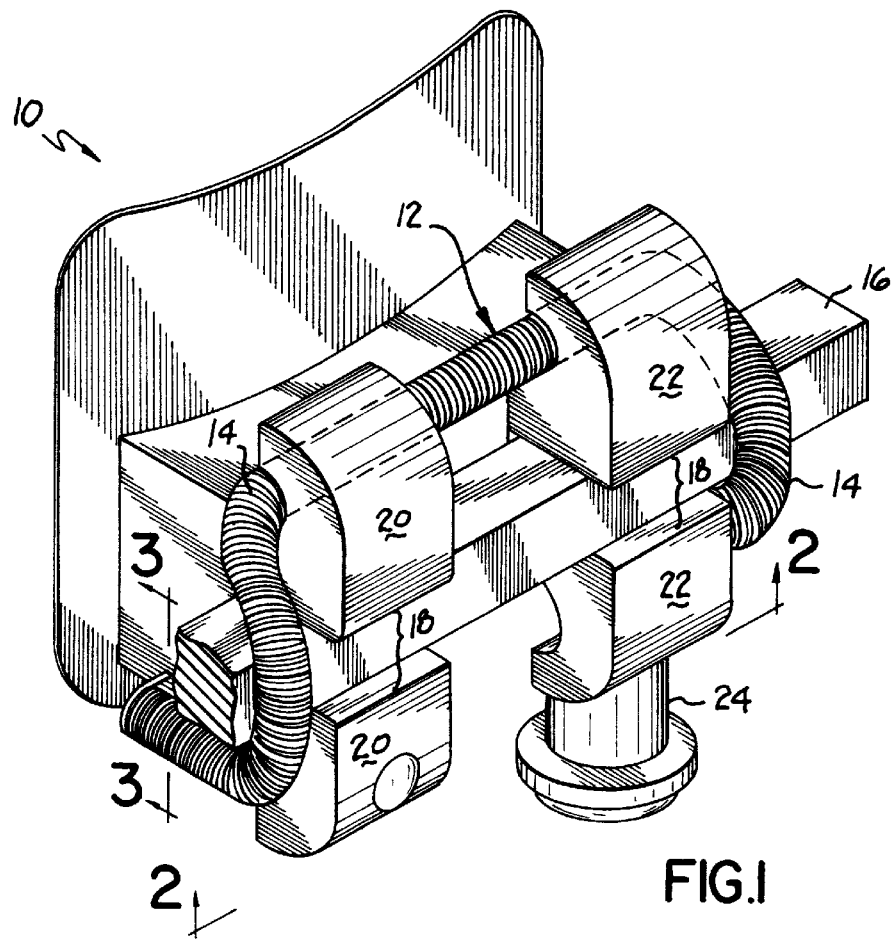
FIG. 1 is a perspective view of one embodiment of a bracket according to the present invention.

With reference to FIG. 1, there is shown an orthodontic bracket 10 having a ligating member 12 comprised of a length of wire and containing a coil spring segment 14 for ligating an archwire 16 in a mesially-distally extending archwire slot 18. The version shown is a labial bracket for use with an archwire. It will be appreciated that the invention is equally applicable to lingual brackets and/or for use in combination with retainer wires. The coil spring segment 14 of ligating member 12 provides extension so that ligating member 12 may be stretched over the archwire 16 and engaged with the occlusally-projecting tie wings 20 and 22. In accordance with the principles of the present invention, the ligating member 12 may be engaged with one or more tie wings, which may be of a gingivally-projecting or occlusally-projecting nature. The bracket may optionally include a hook 24.

Figure 2:
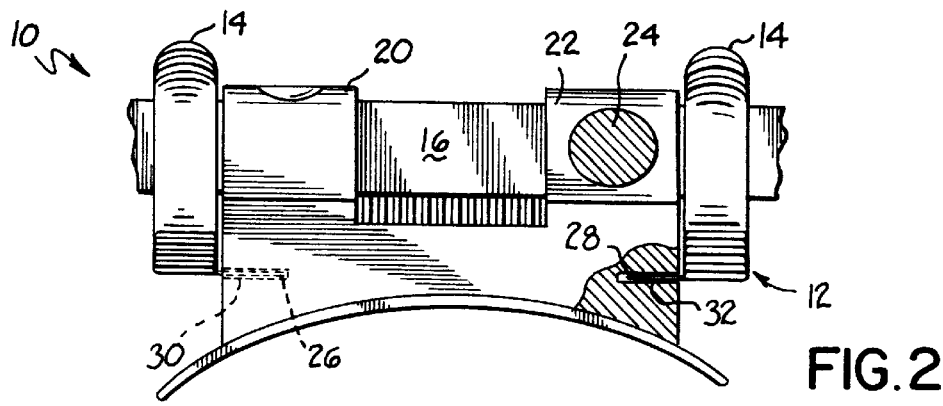
FIG. 2 is a plan view of the gingival side of the bracket shown in FIG. 1.
Figure 3:
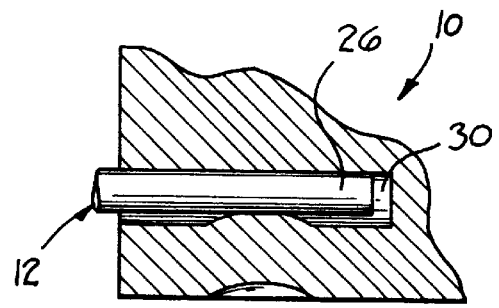
FIG. 3 is a cross-sectional view, taken on line 3—3 of FIG. 1, of a partially cut away section of the bracket shown in FIG. 1.

In one embodiment, as shown more clearly in FIG. 2, ends 26 and 28 of ligating member 12 are straightened and inserted into mesially and distally extending bores 30 and 32. Preferably these straight sections extend for at least 1 mm. Bore 30 opposes bore 32 along the same mesial distal axis in either the gingival or occlusal portion of the bracket body 10, with each bore 30, 32 having a depth of less than one half the length of the bracket body 10. Advantageously, each bore 30, 32 has a depth of at least 0.02 inch, and is more advantageously about 0.05 inch in depth. The diameter of each bore 30, 32 is equal to or greater than the diameter of the wire used for the ligating member. For example, a 0.0075 inch wire may be engaged in a 0.01 inch bore. Advantageously the bore diameter is about 0.0075 to 0.015 inch. Conventional drilling methods, such as laser beam, electron beam or ion beam, or any other suitable process, may be used to form bores 30 and 32. The side of each bore 30, 32 (on the gingival or occlusal side of bracket 10) is staked or punched to deform the bore 30, 32 inside, thus capturing each end 26, 28 of the ligating member 12 in bore 30, 32, as shown in FIG. 3. Any method may be used that results in capturing ends 26, 28 in bores 30, 32.

Figure 4:
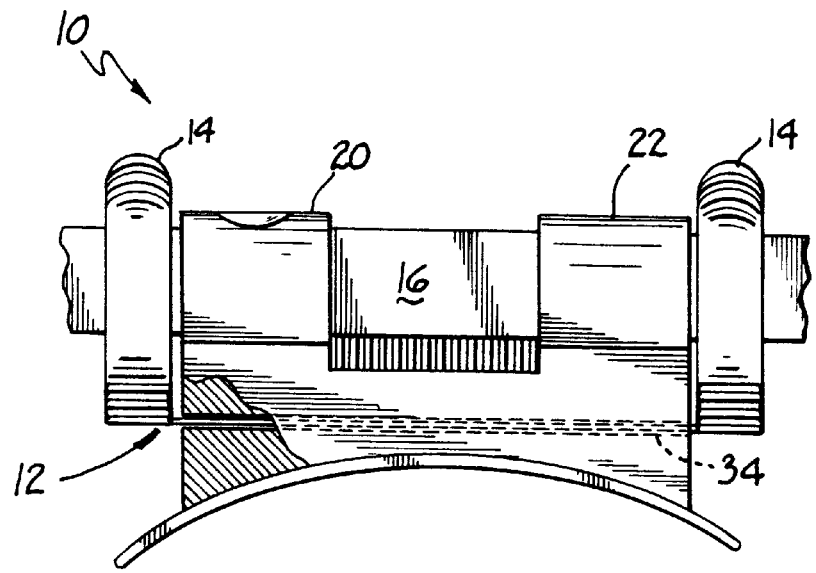
FIG. 4 is a plan view of the gingival side of a second embodiment of the bracket of the present invention.

Alternatively, a closed loop of ligating member 12 may be formed by threading a length of wire of ligating member 12 through a mesially-distally extending bore 34 in the bracket body 10, as shown in FIG. 4. The bore diameter may be the same as that for bores 30 and 32. Bore 34 may extend through the gingival portion or the occlusal portion of bracket body 10. It should be understood that if bores 30, 32 or bore 34 are located in the gingival portion of bracket body 10, then ligating member 12 will be engaged with one or more occlusally-projecting tie wings. On the other hand, if bores 30, 32 or bore 34 are located in the occlusal portion of bracket body 10, then ligating member 12 will be engaged with one or more gingivally-projecting tie wings. Alternatively, ligating member 12 may pass under both the occlusally-projecting and gingivally-projecting tie wings with no portion of the ligating member being passed through a bore, as shown in FIG. 5.

Figure 5:
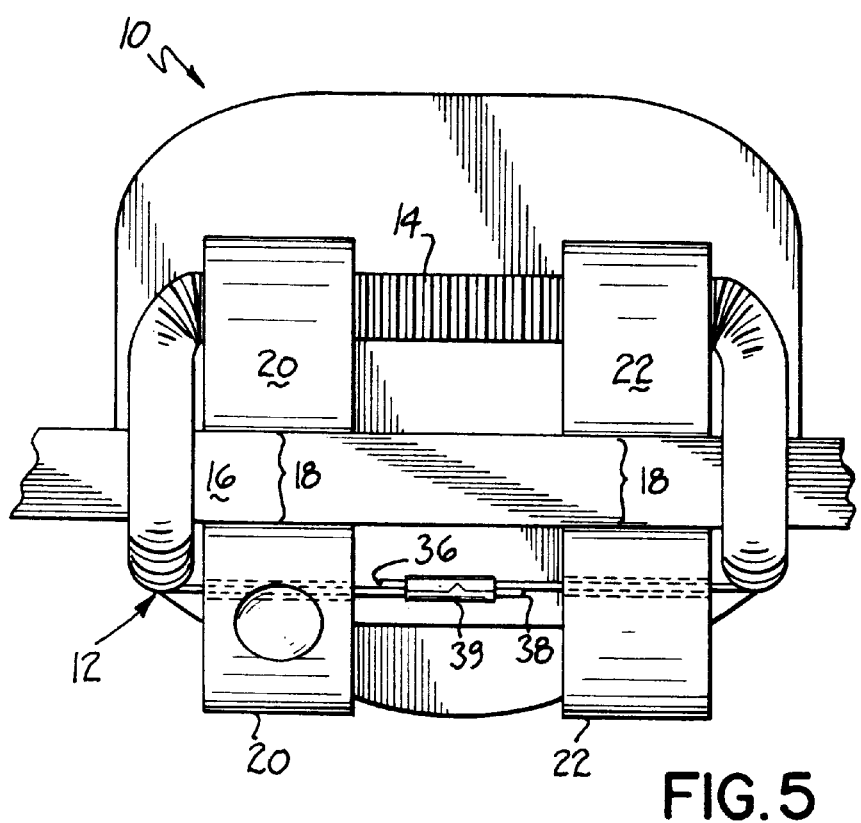
FIG. 5 is a plan view of the labial side of a third embodiment of the bracket of the present invention.
Figure 6:
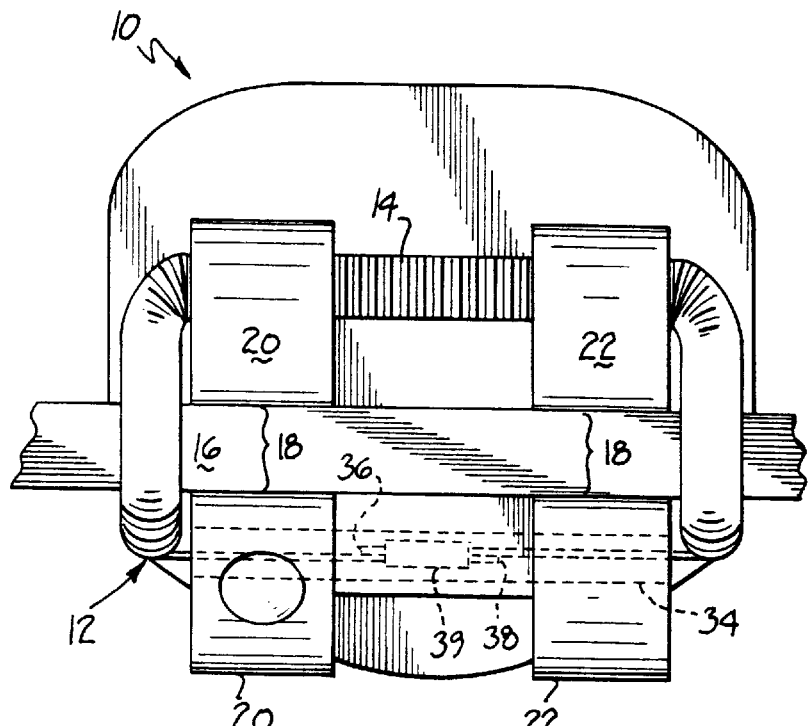
FIG. 6 is a plan view of the labial side of a fourth embodiment of the bracket of the present invention.

Ends 36 and 38 of ligating member 12 may be joined together to form the closed loop, with the joined ends 36 and 38 being located inside of bore 34, as shown in FIG. 6, or at any point outside the bore 34, such as shown in FIG. 5. Ligation member 12 may be made into a closed loop by brazing, welding, clamping or any other chemical, metallurgical or mechanical means or their combination. FIGS. 5 and 6 show a sleeve-type connection 39 for joining the ends 36, 38 of ligation member 12.

Figure 7:
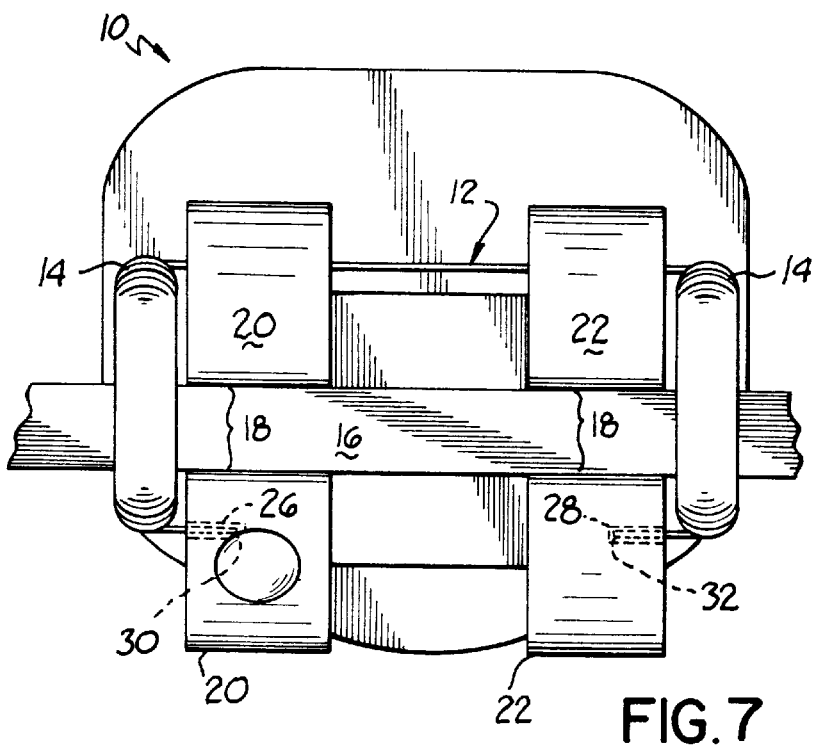
FIG. 7 is a plan view of the labial side of a fifth embodiment of the bracket of the present invention.

Ligating member 12 may be one continuous length of wire or can be more than one piece of wire joined together, as long as the ligation member includes at least one coil spring segment 14. The wire diameter is advantageously 0.005 to 0.015 inch. The coil spring 14 may be located inside bore 34, under the tie wings opposite the portion of bracket body 10 containing bore 34 or bores 30 and 32, over archwire 16 on both the mesial and distal sides of the bracket body 10, as shown in FIG. 7, or in any other location that provides extension for ligating archwire 16 in archwire slot 18. Subsequent to ligation, ligating member 12 with coil spring 14 should provide a continuous force to force archwire 16 to the bottom of archwire slot 18, thus facilitating the desired alignment and preventing unwanted movement or rotation.

Ligating member 12 may be made, in whole or in part, of a Ti-based alloy or of a super elastic or shape memory alloy, such as a Ni/Ti-based alloy, or a Ni—Ti—Nb alloy. The alloy may also contain such elements as Cu, Fe, V, Cr, Co, Ta, Zr and Mo, if desired. Advantageously, the ligating member material, more specifically the material used for the coil spring portion, has an elastic recovery strain twice that of the material used for the bracket body. Advantageously, the elastic recovery stress of the ligating member is in the range of about 100–1000 grams. Typically, the bracket body is made of stainless steel, but could also be made from any other material such as Ti, ceramics, plastics or composites. Any known bracket may be used in accordance with the principles of the present invention.

While the present invention has been illustrated by the description of various embodiments thereof, and while the embodiment has been described in considerable detail, it is not intended to restrict or in any way limit the scope of the appended claims to such detail. Additional advantages and modifications will readily appear to those skilled in the art. For example, the ligating member may be engaged with the bracket body by any method, provided that the ligating member contains at least one coil spring segment. The invention in its broader aspects is therefore not limited to the specific details, representative apparatus and method and illustrative examples shown and described. Accordingly, departures may be made from such details without departing from the scope or spirit of applicant's general inventive concept.

Having described the invention, what is claimed is:

1. An orthodontic bracket comprising:
    a bracket body having a mesially-distally extending slot for receiving an orthodontic wire, and at least one tie wing; and
    a ligating member for ligating an orthodontic wire in said slot, said ligating member engaged within a portion of said bracket body and comprised of a length of wire containing at least one coil spring segment and at least one substantially straight, uncoiled segment spaced from said portion of said bracket body.

2. A bracket according to claim 1 wherein said slot is an archwire slot and said ligating member is adapted to ligate an archwire in said archwire slot.

3. A bracket according to claim 1 wherein said bracket is a lingual bracket.

4. A bracket according to claim 1 wherein said bracket is a labial bracket.

5. A bracket according to claim 4 wherein said at least one tie wing is selected from the group consisting of gingivally-projecting and occlusally-projecting tie wings.

6. A bracket according to claim 1 wherein said bracket body includes a hook.

7. A bracket according to claim 1 wherein the bracket body includes two tie wings.

8. A bracket according to claim 1 wherein the ligating member defines a closed loop.

9. A bracket according to claim 8 wherein said portion of said bracket body has a mesially-distally extending bore therethrough and said ligating member passes through said bore.

10. A bracket according to claim 9 wherein said ligating member is engagable with said at least one tie wing to ligate a wire in said slot.

11. A bracket according to claim 1 wherein said ligating member contains Ti.

12. A bracket according to claim 1 wherein the elastic recovery stress of the ligating member is in the range of about 100–1000 grams.

13. A bracket according to claim 1 wherein said ligating member is made of a material selected from the group consisting of super elastic and shape memory alloys.

14. A bracket according to claim 13 wherein said ligating member is made of a Ni/Ti-based alloy.

15. A bracket according to claim 13 wherein said ligating member is made of a Ni—Ti—Nb alloy.

16. An orthodontic bracket, comprising:

a bracket body having a mesially-distally extending slot for receiving an orthodontic wire and at least one tie wing, said bracket body having two opposed bores therein along a single mesial-distal axis in a gingival portion or an occlusal portion of said bracket body, each said bore extending into said bracket body to a depth of less than one half the length of the bracket body; and a ligating member for ligating an orthodontic wire in said slot, said ligating member engaged within said bores in said bracket body and said ligating member comprised of a length of wire containing at least one coil spring segment and at least one substantially straight, uncoiled segment spaced from said bores in said bracket body.

17. A bracket according to claim 16 wherein said slot is an archwire slot and said ligating member is adapted to ligate an archwire in said archwire slot.

18. A bracket according to claim 16 wherein said bracket is a lingual bracket.

19. A bracket according to claim 16 wherein said bracket is a labial bracket.

20. A bracket according to claim 19 wherein said at least one tie wing is selected from the group consisting of gingivally-projecting and occlusally-projecting tie wings.

21. A bracket according to claim 16 wherein said bracket body includes a hook.

22. A bracket according to claim 16 wherein said bracket body includes two tie wings.

23. A bracket according to claim 16 wherein said ligating member has two ends, each of which is disposed within one of said opposed bores.

24. A bracket according to claim 23, further comprising means for retaining each end of said ligating member in a respective bore in said bracket body.

25. A bracket according to claim 16 wherein said ligating member contains Ti.

26. A bracket according to claim 16 wherein the elastic recovery stress of the ligating member is in the range of 100–1000 grams.

27. A bracket according to claim 16 wherein said ligating member is made of a material selected from the group consisting of super elastic and shape memory alloys.

28. A bracket according to claim 27 wherein said ligating member is made of a Ni—Ti—Nb alloy.

29. A bracket according to claim 16 wherein said ligating member is made of a Ni/Ti-based alloy.

30. An orthodontic bracket, comprising:

a bracket body having a mesially-distally extending slot for receiving an orthodontic wire and at least one tie wing, said bracket body having two opposed bores therein along a single mesial-distal axis in a gingival portion or an occlusal portion of said bracket body, each said bore extending into said bracket body to a depth of less than one half the length of the bracket body; and a ligating member for ligating an orthodontic wire in said slot, said ligating member comprising a length of wire containing at least one coil spring segment and opposing ends, each said opposing end retained within one of said bores in said bracket body by a crimp which deforms a portion of said bracket body into each of said bores.

* * * * *